(12) United States Patent
Biedermann et al.

(10) Patent No.: US 9,333,016 B2
(45) Date of Patent: May 10, 2016

(54) POLYAXIAL BONE ANCHORING DEVICE

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Timo Biedermann, Trossingen (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 72 days.

(21) Appl. No.: 13/933,777

(22) Filed: Jul. 2, 2013

(65) Prior Publication Data

US 2014/0012337 A1    Jan. 9, 2014

Related U.S. Application Data

(60) Provisional application No. 61/667,670, filed on Jul. 3, 2012.

(30) Foreign Application Priority Data

Jul. 3, 2012 (EP) .................................. 12174846

(51) Int. Cl.
*A61B 17/70* (2006.01)
*A61B 17/84* (2006.01)

(52) U.S. Cl.
CPC ............ *A61B 17/844* (2013.01); *A61B 17/7032* (2013.01); *A61B 17/7037* (2013.01)

(58) Field of Classification Search
CPC ..................... A61B 17/7037; A61B 17/7032
See application file for complete search history.

(56) References Cited

U.S. PATENT DOCUMENTS 5,882,350 A * 3/1999 Ralph ................ A61B 17/7032
                                                      606/278
6,063,090 A * 5/2000 Schlapfer ........... A61B 17/7041
                                                      606/270

(Continued)

FOREIGN PATENT DOCUMENTS

EP          2 462 886 A1    6/2012
WO    WO 2011/077511 A1    6/2011
WO    WO 2012/088890 A1    7/2012

OTHER PUBLICATIONS

Extended European Search Report for European Application No. 12174846.1, European Search Report dated Nov. 7, 2012 and mailed Nov. 14, 2012 (6 pgs).

(Continued)

*Primary Examiner* — David Bates
(74) *Attorney, Agent, or Firm* — Lewis Roca Rothgerber Christie LLP (57) ABSTRACT

A receiving part of a polyaxial bone anchoring device includes a first member with a top end and a bottom end, a central axis, a head receiving portion having an inner wall defining a passage at the bottom end for introducing a head of a bone anchoring element, and a channel at the top end for receiving a rod, a second member having a bore and being connectable to the first member at the bottom end of the first member; and at least one clamping member configured to be positioned at or near the bottom end of the first member and to protrude into the passage. The second member is movable relative to the first member from a first position wherein the clamping member is movable radially, to a second position wherein the clamping member is prevented from moving, to hold a head of a bone anchoring element therein.

23 Claims, 7 Drawing Sheets

(56) References Cited

U.S. PATENT DOCUMENTS

| | | | | |
|---|---|---|---|---|
| 6,248,105 | B1* | 6/2001 | Schlapfer | A61B 17/7032 606/266 |
| 7,316,684 | B1* | 1/2008 | Baccelli | A61B 17/7037 606/86 A |
| 8,506,609 | B2* | 8/2013 | Biedermann | A61B 17/7037 606/266 |
| 9,060,814 | B2* | 6/2015 | Doubler | A61B 17/704 |
| 9,144,441 | B2* | 9/2015 | Biedermann | A61B 17/7076 |
| 2006/0036252 | A1* | 2/2006 | Baynham | A61B 17/7035 606/308 |
| 2006/0241600 | A1 | 10/2006 | Ensign et al. | |
| 2006/0247631 | A1* | 11/2006 | Ahn | A61B 17/7037 606/272 |
| 2007/0043358 | A1 | 2/2007 | Molz, IV et al. | |
| 2007/0123862 | A1 | 5/2007 | Warnick | |
| 2008/0015576 | A1* | 1/2008 | Whipple | A61B 17/7037 606/60 |
| 2008/0015579 | A1* | 1/2008 | Whipple | A61B 17/7037 606/250 |
| 2008/0045963 | A1* | 2/2008 | Abdou | 606/73 |
| 2008/0108992 | A1* | 5/2008 | Barry | A61B 17/7037 606/258 |
| 2008/0208256 | A1* | 8/2008 | Thramann | A61B 17/70 606/246 |
| 2010/0036433 | A1 | 2/2010 | Jackson | |
| 2010/0168800 | A1* | 7/2010 | Biedermann et al. | 606/302 |
| 2011/0208248 | A1* | 8/2011 | Barrus et al. | 606/305 |
| 2012/0179209 | A1* | 7/2012 | Biedermann et al. | 606/305 |
| 2012/0197314 | A1* | 8/2012 | Farris | A61B 17/7037 606/305 |
| 2012/0209335 | A1* | 8/2012 | Termyna | A61B 17/7037 606/300 |
| 2012/0310284 | A1* | 12/2012 | Gerchow | A61B 17/7037 606/264 |
| 2013/0053901 | A1* | 2/2013 | Cormier et al. | 606/305 |
| 2013/0110180 | A1* | 5/2013 | Doubler et al. | 606/308 |

OTHER PUBLICATIONS

Search of the Austrian Patent Office by Serv.ip, "Ihr Partner für Forschung und Innovation Express-Recherche zum Stand der Technik," dated Aug. 8, 2012, 6 pp.

\* cited by examiner

POLYAXIAL BONE ANCHORING DEVICE

CROSS-REFERENCE TO RELATED APPLICATION(S)

The present application claims priority to and the benefit of U.S. Provisional Patent Application Ser. No. 61/667,670, filed Jul. 3, 2012, the contents of which are hereby incorporated by reference in their entirety, and claims priority from European Patent Application EP 12 174 846.1, filed Jul. 3, 2012, the contents of which are hereby incorporated by reference in their entirety.

BACKGROUND

1. Field

The invention relates to a polyaxial bone anchoring device. The anchoring device includes an anchoring element having a shank and a head and further includes a receiving part for coupling the anchoring element to a rod. The receiving part has an upper member and a lower member connectable to the upper member and at least one clamping member that is configured to hold the anchoring element in the receiving part when the upper and lower members are assembled. The polyaxial bone anchoring device is particularly suitable for providing a modular system.

2. Description of Related Art

WO 2011/077511 A1 describes a spine fixing device provided with a screw and also with a head to which the screw and a rod can be fixed. The head is provided with a head body and a fixing nut, which fixes the screw to the head. When mounted to the head body, the fixing nut holds the screw. The state of mounting of the fixing nut to the head body is adapted to be switchable between a first state, in which the screw is held so as to be able to pivot and a second state, in which the screw is held, so as not to be able to pivot.

SUMMARY

It is the object of the invention to provide a polyaxial bone anchoring device that is improved in view of its handling and in view of the variety of applications of the device.

The polyaxial bone anchoring device is a bottom-loading type polyaxial bone anchoring device that allows to insert the anchoring element from the bottom of the receiving part. Due to this design, a modular system can be provided, wherein a single receiving part can be combined with various anchoring elements. The anchoring elements may differ in view of their shank length, shank diameter, anchoring type, such as screws, nails or other bone anchors. By means of such a modular system, the bone anchoring device can be used in a broad variety of clinical situations. This gives the surgeon a substantial choice of implants and reduces the number of parts that are included in an implant set or configuration.

The bone anchoring device can be easily assembled. A stop for the head of the bone anchoring elements is provided in the receiving part and allows to correctly position the head of the anchoring element in the receiving part.

The at least one clamping member and the stop provide for a friction fit of the head within the receiving part so that the head can be held in the receiving part in an adjustable angular position. The friction force can be overcome manually by pivoting the receiving part relative to the anchoring element, so that a plurality of bone anchoring devices can be easily aligned to receive the rod, which is to be inserted.

BRIEF DESCRIPTION OF DRAWINGS

Further features and advantages of the invention will become apparent from the description of embodiments by means of the accompanying drawings. In the drawings:

FIG. 10b shows an enlarged portion of FIG. 10a;

FIG. 11b shows an enlarged portion of FIG. 11a;

FIG. 12a shows a cross-sectional view of a further step of assembling the bone anchoring device according to the first embodiment, wherein the lower member is being connected to the upper member;

FIG. 12b shows an enlarged portion of FIG. 12a;

FIG. 13b shows an enlarged view of a portion of FIG. 13a;

FIG. 14b shows an enlarged view of a portion of FIG. 14a;

FIG. 22b shows an enlarged view of a portion of FIG. 22a; and

DETAILED DESCRIPTION

Figure 1:
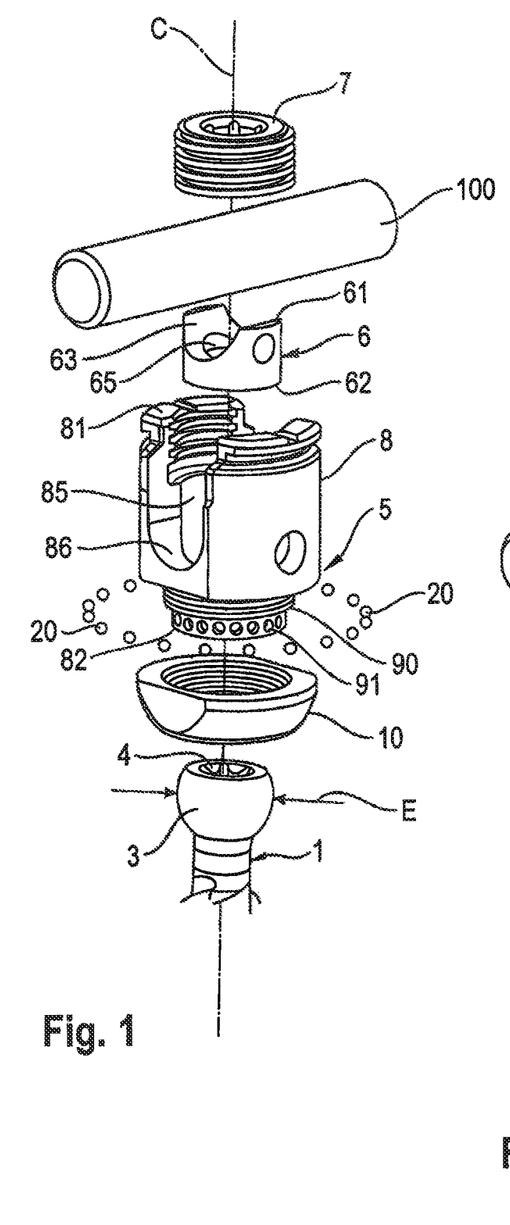
FIG. 1 shows a perspective exploded view of the bone anchoring device according to a first embodiment.
Figure 2:
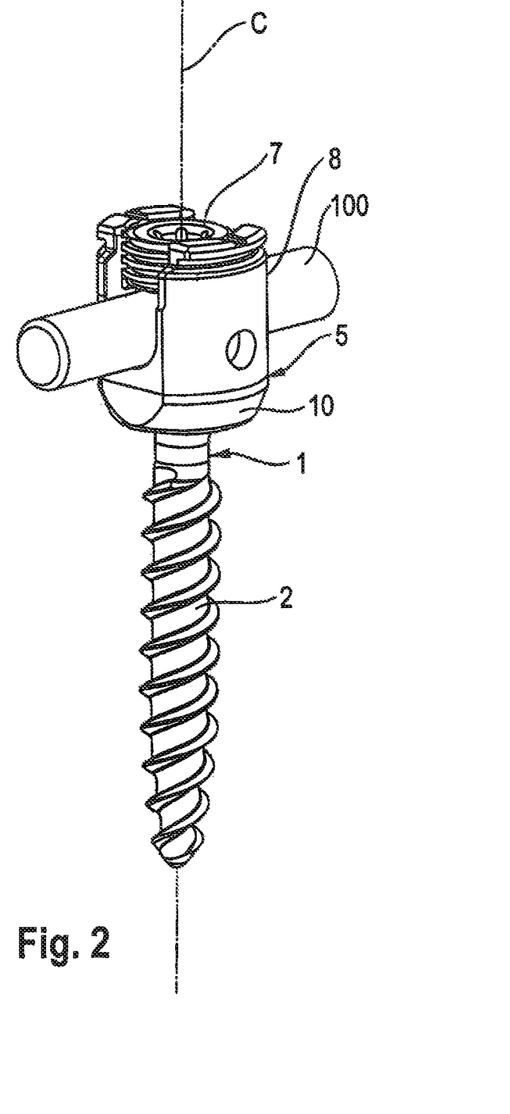
FIG. 2 shows a perspective view of the bone anchoring device of FIG. 1 in an assembled state.
Figure 3:
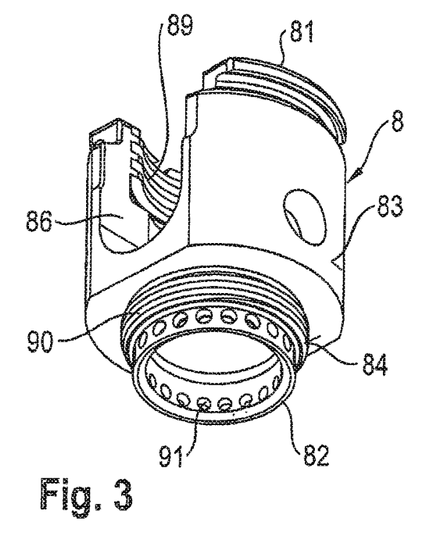
FIG. 3 shows a perspective view from the bottom of an upper member of the receiving part according to the first embodiment.
Figure 4:
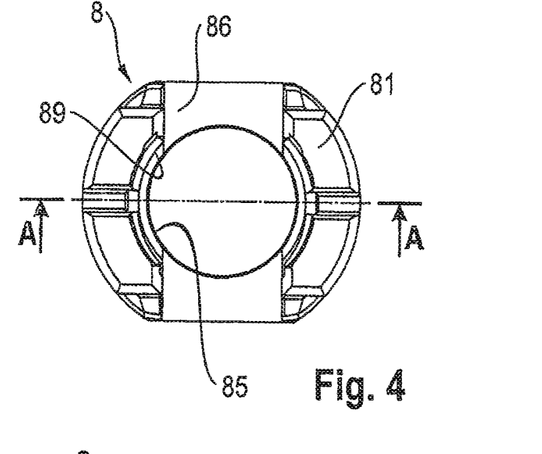
FIG. 4 shows a top view of the receiving part according to the first embodiment.
Figure 5:
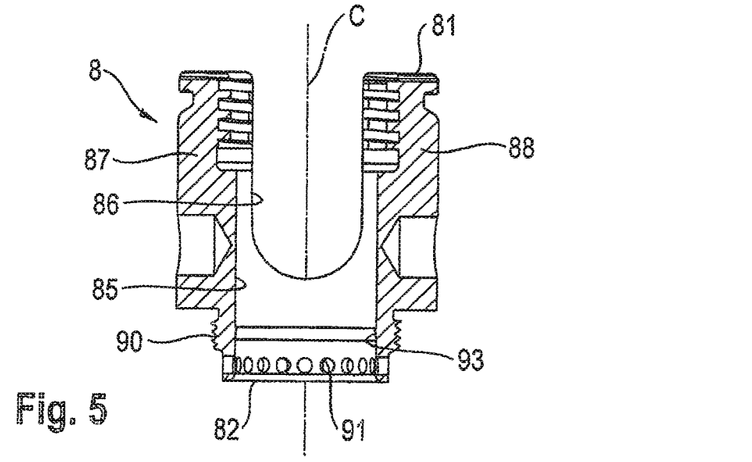
FIG. 5 shows a cross-sectional view of the upper member of the receiving part along line A-A in FIG. 4.

As shown in FIGS. 1 and 2, the polyaxial bone anchoring device according to a first embodiment comprises a bone anchoring element 1 in the form of a bone screw having a shank 2 with a threaded portion and a spherical segment-shaped head 3. The head 3 includes a region with a largest diameter E of the sphere and comprises a recess 4 for engagement with a screwdriver. The bone anchoring device further includes a receiving part 5 for receiving the head 3 of the anchoring element 1 and for receiving a rod 100 in order to couple the bone anchoring element 1 to the rod 100. In the receiving part 5, a pressure element 6 is arranged for exerting pressure onto the head 3, when the head 3 is inserted into the receiving part 5. In addition, the bone anchoring device comprises a locking element 7 for securing the rod 100 and for locking the head 3 in the receiving part 5.

As shown in FIG. 1, the receiving part 5 includes an upper member 8 and a lower member 10 that is connectable to the upper member 8. Referring further to FIGS. 3 to 6, the upper member 8 has a top end 81 and an opposite bottom end 82. Adjacent to the top end 81, there is a first substantially cylindrical portion 83 with a first maximum outer diameter, and adjacent to the bottom end 82, there is a second substantially cylindrical portion 84 with a second diameter that is smaller than the first diameter. The second portion 84 acts as a head receiving portion. Due to its symmetry, the upper member 8 comprises a central axis C extending through the upper member 8 from the top end 81 to the bottom end 82. The upper member 8 further has a coaxial passage 85 extending completely through the member from the top end 81 to the bottom end 82. The passage 85 may be a bore that may have different inner diameters along the axial direction. A substantially U-shaped recess 86 is provided adjacent to the top end by means of which two upstanding free legs 87, 88 are formed that are the sidewalls of a channel for receiving the rod 100. At or near the top end 81 an internal thread 89 is provided for engagement with the locking element 7. The first portion 83 may have opposite flat sides in a plane perpendicular to the channel axis to reduce the overall dimensions of the receiving part.

Figure 6:
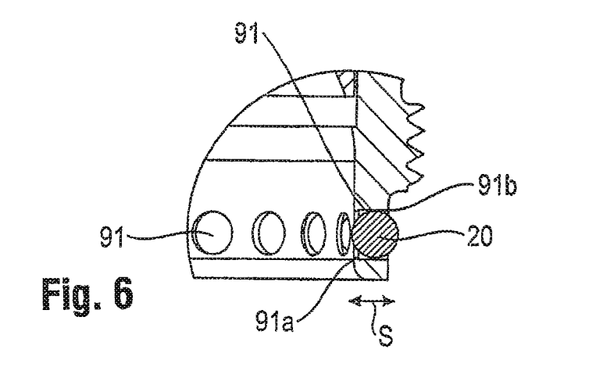
FIG. 6 shows a cross-sectional view of an enlarged portion of the upper member with a ball inserted into a bore provided in the upper member.

The second portion 84 of the upper member 8 comprises a threaded outer surface portion 90 adjacent to or closest to the first substantially cylindrical portion 83. Between the threaded outer surface portion 90 and the bottom end 82, a plurality of transverse bores 91 are provided at circumferentially equidistant positions. The bores 91 extend fully through the wall of the second cylindrical portion 84. Each bore 91 has a region 91a with a gradually reducing inner diameter near the inner wall of the upper member 8, in other words, an inner bevelled section, so that the diameter of the bores 91 at the inner wall are slightly reduced. As can be seen in particular in FIG. 6, each bore 91 is configured to receive a ball 20 therein. While FIG. 6 shows only one ball 20 received in a bore 91, a plurality of balls 20 is provided, as can be seen in FIG. 1. The inner diameter of the bores 91 is such that the balls 20 can rotate in the bores 91. When the balls 20 are placed into the bores 91, respectively, the outer edge 91b of the bores may be crimped to hold the balls 20 within the bores 91. The balls 20 that are confined in this way within the bores 91, are configured to slide to some extent in a transverse direction as indicated by the double arrow S in FIG. 6. Hence, when sliding in the direction towards the center of the upper member 8, the balls 20 can protrude into the passage 85.

The inner wall of the passage 85 comprises at a distance from the bottom end 82 a protrusion 93. The protrusion 93 is annular and spherically rounded such that it fits to the head 3 of the anchoring element 1. The protrusion 93 is at such a distance from the bottom end 82, that when the head 3 abuts against it, the bores 91 with the balls 20 are at a position below the region with the greatest diameter E of the head 3. Further, the head 3 protrudes into the passage 85 above the protrusion 93 so that it can be contacted by the pressure element 6.

Figure 7:
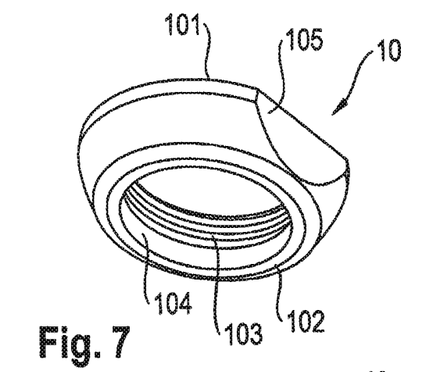
FIG. 7 shows a perspective view from the bottom of the lower member of the receiving part according to the first embodiment.
Figure 8:
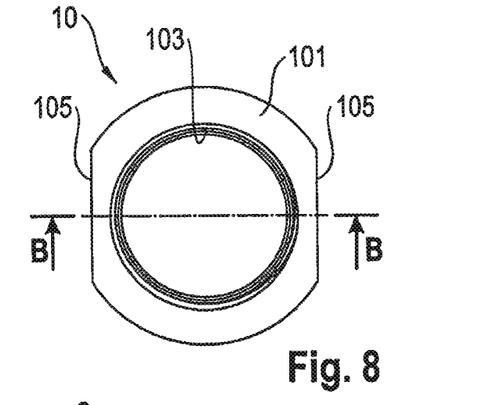
FIG. 8 shows a top view of the lower member shown in FIG. 7.
Figure 9:
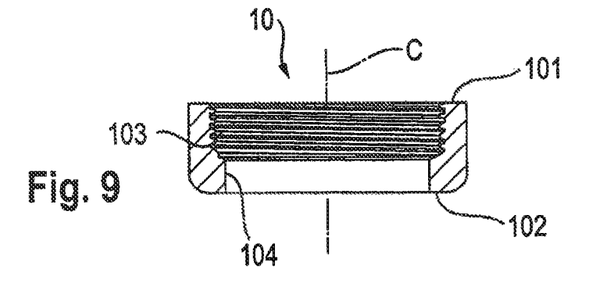
FIG. 9 shows a cross-sectional view of the lower member according to line B-B in FIG. 8.

Referring in particular to FIGS. 7 to 9, the lower member 10 is a substantially sleeve-shaped part that has a top end 101 and an opposite bottom end 102 and a passage that extends fully from the top end 101 to the bottom end 102. The passage comprises a first portion 103 with an internal thread that cooperates with the external thread of the threaded portion 90 of the upper member 8. Between the first portion 103 and the bottom end 102, there is a second portion 104 that is threadless and that has a slightly larger inner diameter than the outer diameter of the wall of the second portion 84 having the bores 91 of the upper member 8. More in detail, the outer diameter of the second portion 104 of the passage has such a size that the lower member 10 is configured to displace the balls 20, when they are seated in the holes 91, towards the inside of the upper member 8 in a radial direction.

The outer surface of the lower member 10 adjacent to the first end 101 may be flush with the outer surface of the upper member 8 when the lower member 10 is mounted to the upper member 8 and may be tapering towards the second end 102, for example in a rounded manner. The inner diameter of the passage at any portion of the lower member 10 is larger than the outer diameter of the shank 2 and is also larger than the maximum outer diameter E of the head 3 of the bone anchoring element 1. Furthermore, the lower member 10 may have flat surface portions 105 arranged on opposite sides that facilitate gripping of the lower member 10, when the lower member 10 is to be mounted to the upper member 8. Preferably, the flat surface portion 105 correspond to flat surface portion of the upper member 8 in the fully assembled state as shown in FIG. 2 to reduce the dimension of the polyaxial bone anchoring device in a direction along the rod axis.

Figure 10A:
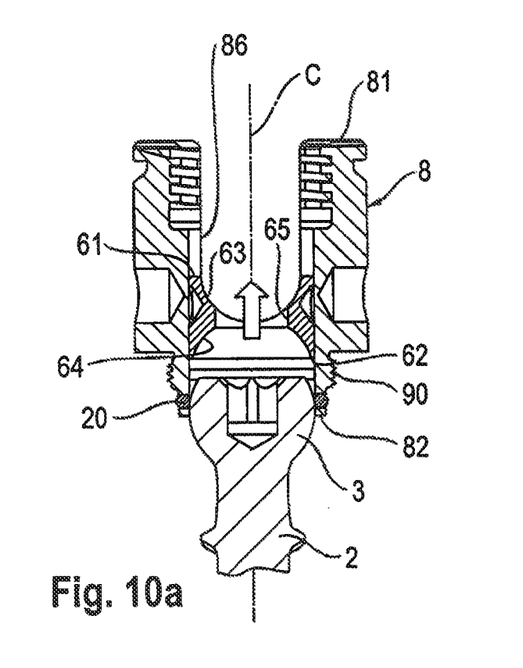
FIG. 10a shows a cross-sectional view of a first step of assembling the polyaxial bone anchoring device according to the first embodiment.

The pressure member 6 will now be explained with reference to FIGS. 1 and 10a. The pressure member 6 is a substantially cylindrical part with a top end 61 and an opposite bottom end 62. Adjacent to the top end 61, there is a substantially cylindrical recess 63 for receiving the rod 100. Adjacent to the bottom end 62, there is a substantially spherical segment-shaped recess 64 that has a radius corresponding to the radius of the head 3 so that when the pressure member 6 is placed onto the head 3 and pressed downward, the load is distributed onto the head 3. Furthermore, a coaxial through-hole 65 is provided for allowing access to the recess 4 of the head 3 of the bone anchoring element 1.

The parts of the polyaxial bone anchoring device are made of a bio-compatible material. In particular, they can be made of bio-compatible metal, such as titanium, a bio-compatible alloy, such as, for example, Nitinol or of a bio-compatible plastic material, such as for example, PEEK (polyetheretherketone). The parts can be made all of the same or of different materials.

Figure 10B:
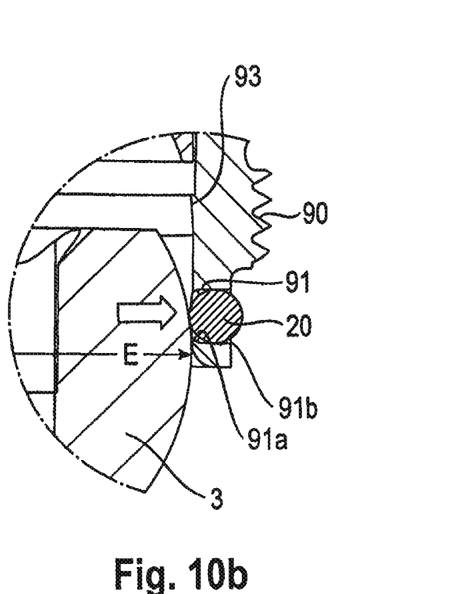

The assembly of the polyaxial bone anchoring device according to the first embodiment will now be described with reference to FIGS. 10a to 14b. First, as shown in FIGS. 10a and 10b, the upper member 8 is provided together with the pressure element 6 in a pre-assembled manner. The pressure element 6 is arranged in the upper member 8 such that the spherical segment-shaped recess 64 is oriented towards the bottom end 82. The pressure element 6 may be temporarily held and aligned in the upper member 8 through, for example, crimping. The balls 20 are inserted into the bores 91 and held therein. The bone anchoring element is introduced with the head 3 through the bottom end 82 of the upper member 8 into the passage 85 of the upper member 8. When the head 3 passes the region with the balls 20, the balls 20 are shifted by the head 3 towards the outside to allow the head 3 to pass, as shown in FIG. 10b.

Figure 11A:
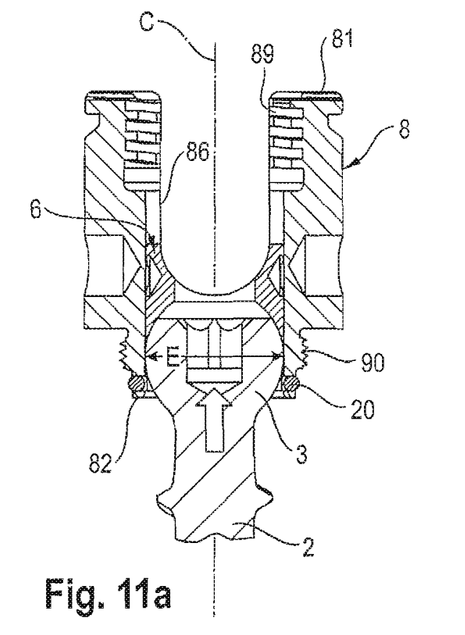
FIG. 11a shows a cross-sectional view of a next step of assembling the polyaxial bone anchoring device according to the first embodiment.
Figure 11B:
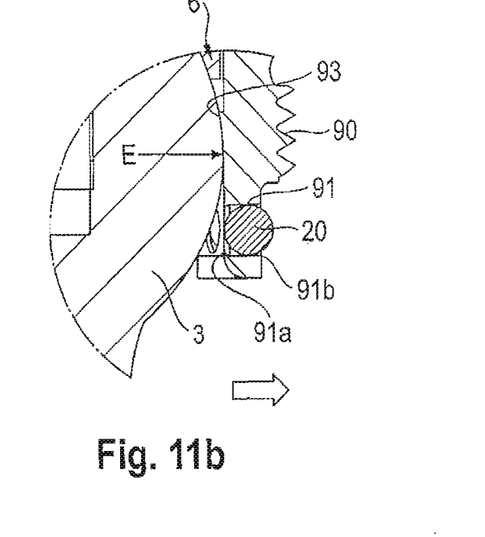

Next, as shown in FIGS. 11a and 11b, the head 3 is farther introduced into the passage 85 until it abuts against the protrusion 93 and is prevented from further moving upwards. In this configuration, the balls 20 are arranged relative to the head 3 at a position below the greatest diameter E of the head 3. The balls 20 are in the outermost position where their surface portions that are oriented toward the inside are flush with or behind the inner wall of the upper member 8 that surrounds the bores 91.

Figures 12A, 12B:
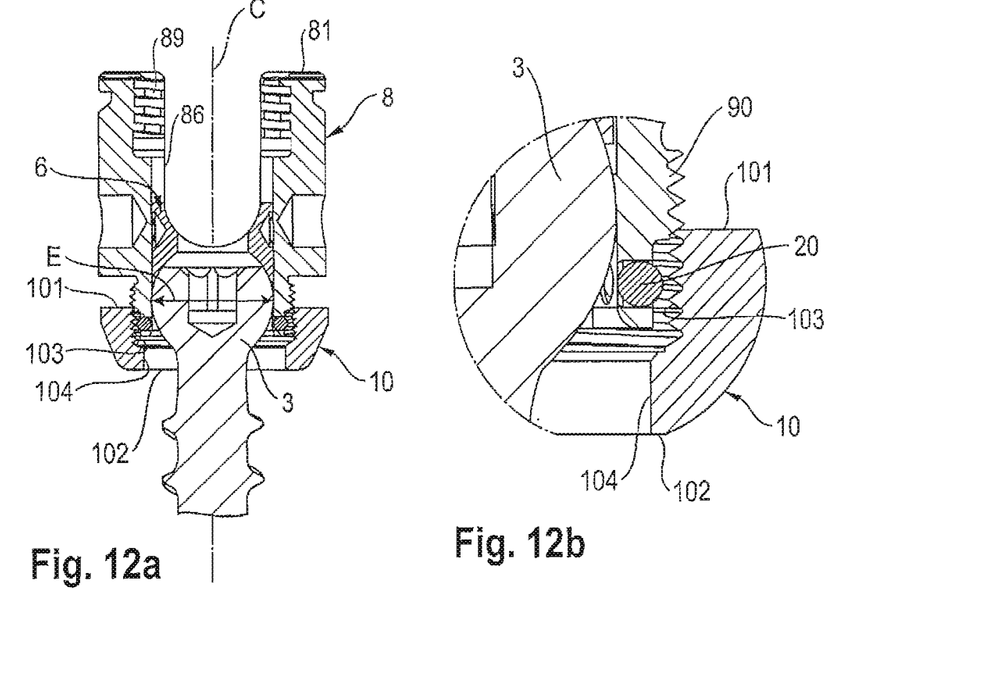

As shown in FIGS. 12a and 12b, the lower member 10 is mounted to the upper member 8 by orienting it with its top end 101 towards the upper member 8 and screwing it onto the threaded portion 90 of the upper member 8.

Figure 13A:
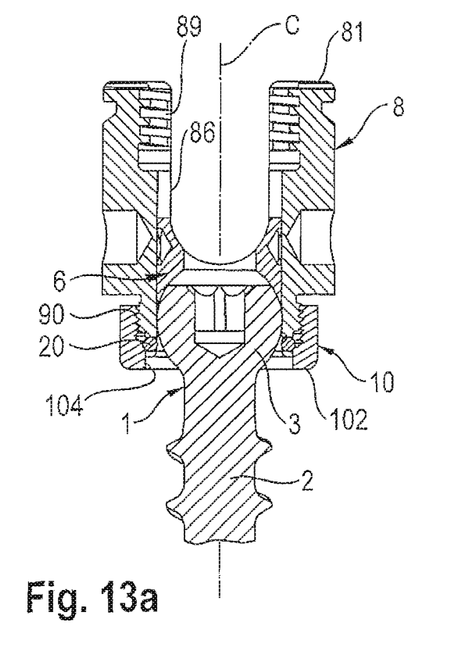
FIG. 13a shows a further step of assembling a polyaxial bone anchoring device according to the first embodiment, wherein the lower member is being screwed onto the upper member.
Figure 13B:
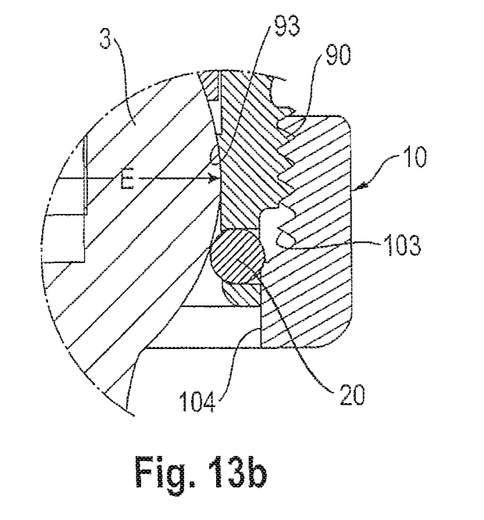

As can be seen in FIGS. 13a and 13b, when the second, threadless portion 104 of the passage of the lower member 10 passes the balls 20, the balls 20 that were protruding outside are shifted by the second portion 104 towards the inside of the passage 85 of the upper member 8 to such an extent that a portion of the balls 20 protrudes into the passage 85 of the upper member 8, thereby reducing the diameter of the passage 85 at this position. Because the inner diameter of the passage 85 corresponds substantially to the largest diameter F of the head 3, the reduction of the inner diameter of the passage 85 through the balls 20 prevents the head 3 from being removed through the bottom end 82 as soon as the portion 104 has shifted the balls 20 towards the inside. This holds the head 3 in place within the upper member 8.

Figure 14A:
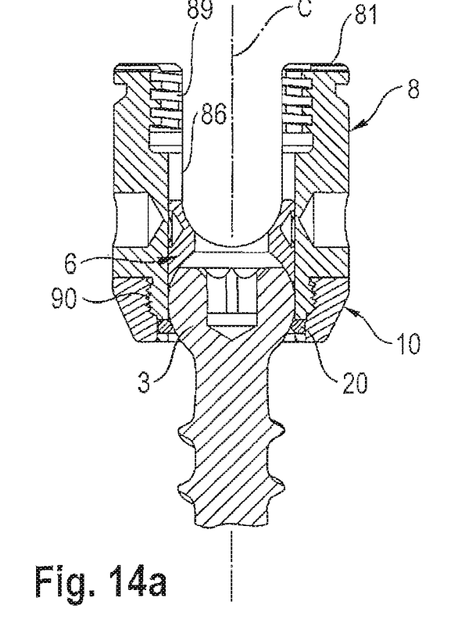
FIG. 14a shows a cross-sectional view of a final step of assembling the polyaxial bone anchoring device according to the first embodiment.
Figure 14B:
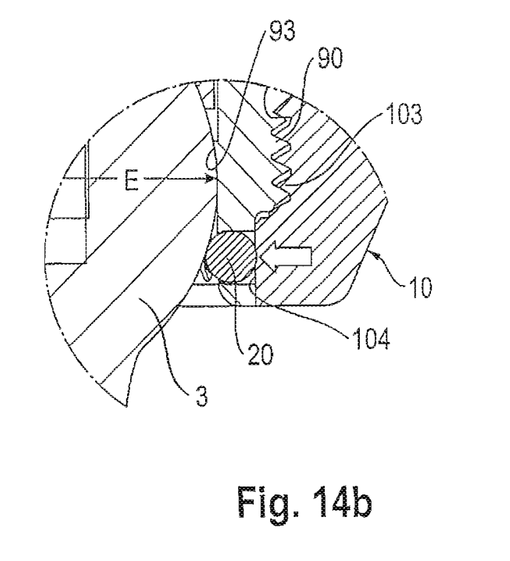

Finally, as shown in FIGS. 14a and 14b, the lower member is mounted to the upper member until its top end 101 abuts against the first cylindrical portion 83 of the upper member 8. In this configuration, the head 3 of the bone anchoring element 1 is pivotably held in the upper member 8 through the action of the lower member 10 that keeps the balls 20 at the inside position. Depending on the dimensions of the bores 91 with the balls 20 relative to the head 3, the balls 20 exert a slight pressure onto the head 3 so that a friction force is generated between the head 3 and the balls 20 on the one hand, and between the head 3 and the protrusion 93 on the other hand. Hence, the head 3 is held under preload in an adjustable angular position. A force greater than the friction force is necessary to pivot the upper member 8 and lower member 10 relative to the bone anchoring element 1. This facilitates handling during surgery.

In use, at least two polyaxial bone anchoring devices are inserted into the bone, for example, into the pedicles of adjacent vertebrae. The receiving parts consisting of the upper members and the lower members are pivoted relative to the bone anchoring elements until they are aligned to received the rod 100. Then, the rod 100 is inserted and the locking elements 7 are screwed between the legs 87, 88 of the upper members 8 and tightened until they press onto the rod 100. The pressure force is transferred via the pressure elements 6 to the heads 3 and the whole assembly is locked.

Referring now to FIGS. 15 to 20, a polyaxial bone anchoring device according to a second embodiment comprises the bone anchoring element 1, a receiving part 5' with an upper member 8', a lower member 10' and a clamping member in the form of a clamping ring 200 as well as the pressure element 6 and the locking element 7 (not shown). Portions that are identical to the portions of the first embodiment, are indicated with the same reference numerals and the description thereof is not repeated.

Figure 16:
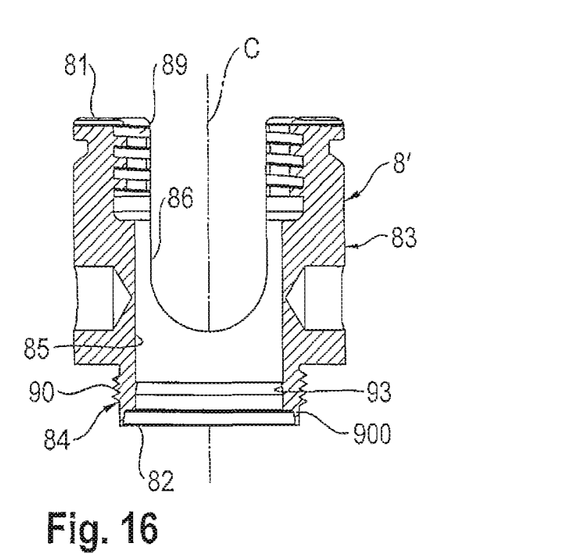
FIG. 16 shows a cross-sectional view of the upper member shown in FIG. 15, the section taken in a plane perpendicular to the rod axis.
Figure 17:
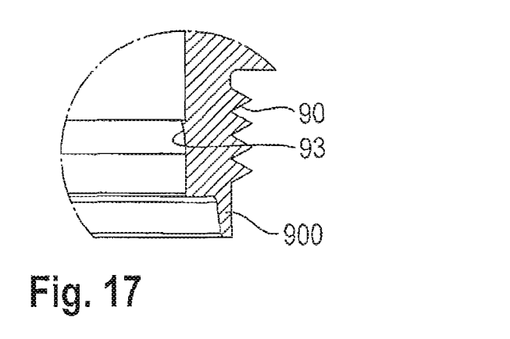
FIG. 17 shows an enlarged view of a portion of FIG. 16.
Figure 18:
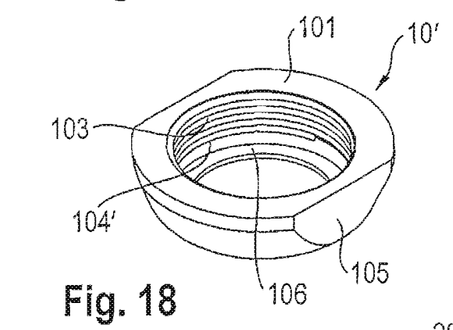
FIG. 18 shows a perspective view from the top of the lower member of the receiving part according to the first embodiment.
Figure 19:
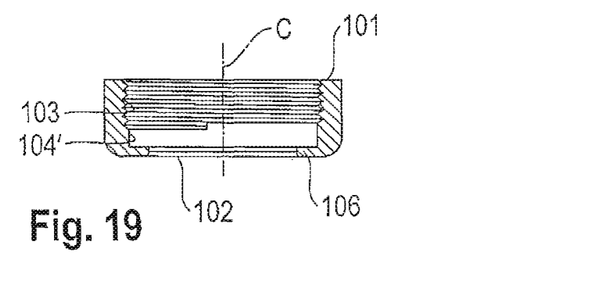
FIG. 19 shows a cross-sectional view of the lower member of FIG. 18.

As shown in FIGS. 16 and 17, the head receiving portion 84 of the upper member 8' comprises adjacent to the bottom end 82 an annular section 900 that has an inner surface conically widening towards the bottom end 82 and with a diameter greater than the inner diameter of the passage below the protrusion 93. The conical shape is used to generate a gradually increasing compression force in a radial direction onto the clamping ring 200 as described below.

The lower member 10' has as in the first embodiment a first portion 103 with an internal thread and adjacent to the first portion, a second portion 104' of the passage with a hollow cylindrical shape that is substantially adapted in the dimension to the outer contour of the second portion 900 of the upper member 8' so that when the lower member 10' is mounted to the upper member 8', the second portion 900 of the upper member 8' fits into the second portion 104' of the lower member 10'.

At the second end 102, the lower member 10' comprises an inwardly protruding edge 106 that limits the inner diameter of the passage at the bottom end 102 to substantially the maximum diameter E of the head 3.

Figure 15:
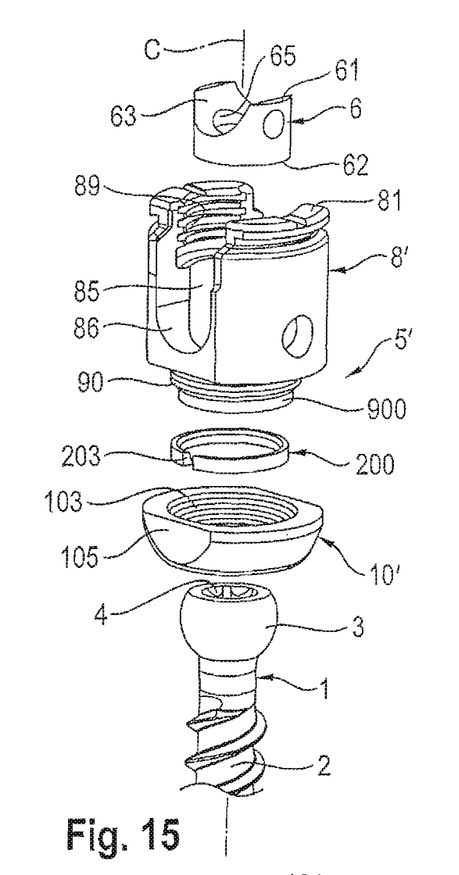
FIG. 15 shows a perspective exploded view of the polyaxial bone anchoring device according to a second embodiment.
Figure 20:
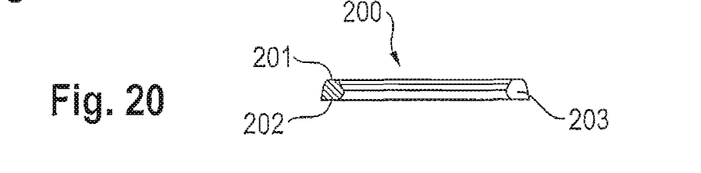
FIG. 20 shows a cross-sectional view of a clamping ring of the polyaxial bone anchoring device according to the second embodiment, the section taken along a plane containing the central axis and a slot of the clamping ring.

As can be seen in particular in FIGS. 15 and 20, the clamping ring 200 has a top end 201, a bottom end 202 and a slot 203. The slot 203 renders the clamping ring 200 compressible in a radial direction. As can be seen in particular in FIG. 20 and FIG. 21, the clamping ring 200 is preferably pre-assembled with the lower member 10' in such a way that it rests on the inwardly protruding edge 106 of the lower member 10' with its lower end 202. The size of the clamping ring 200 is such that when the clamping ring 200 rests on the lower edge 106, it is not or not fully compressed so that the slot 203 is still open. The cross-section of the clamping ring 200 is rounded towards the central axis, even at the bottom end 202 and conically widening from the top end 201 towards the bottom end 202 at the outside such that as can be seen in particular in FIG. 21, it substantially fits into the second portion 104' of the lower member 10' and is held therein.

Figure 21:
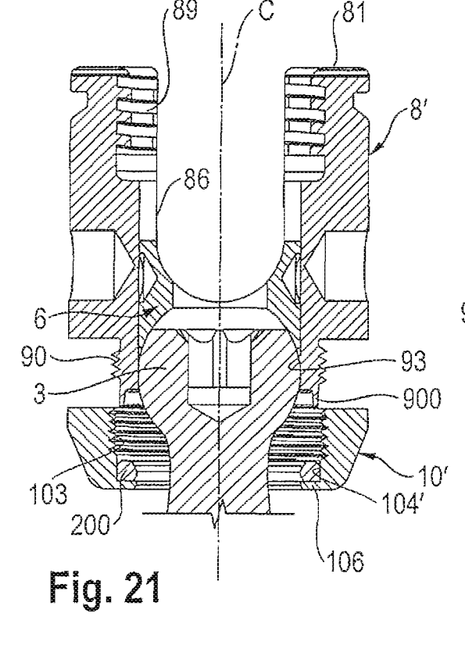
FIG. 21 shows a cross-sectional view of a first step of assembling the polyaxial bone anchoring device according to the second embodiment.
Figure 22A:
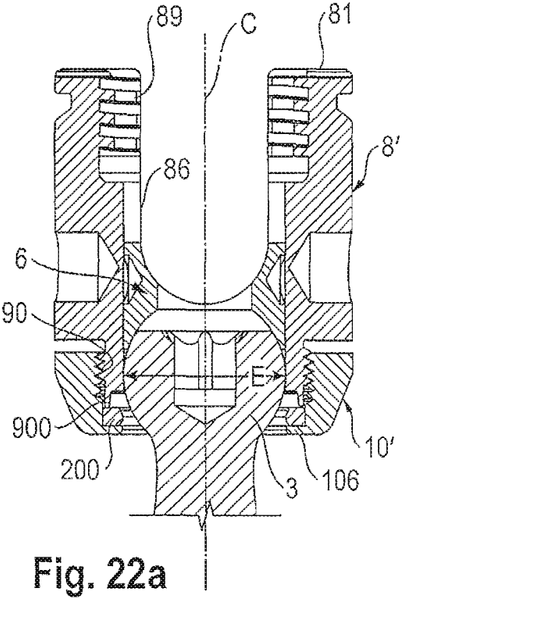
FIG. 22a shows a further step of assembling the polyaxial bone anchoring device according to the second embodiment.
Figure 22B:
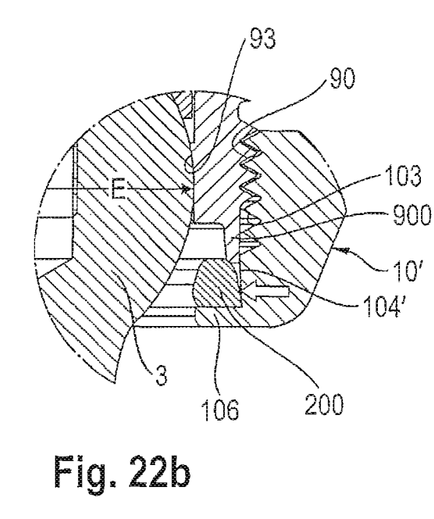
Figure 23:
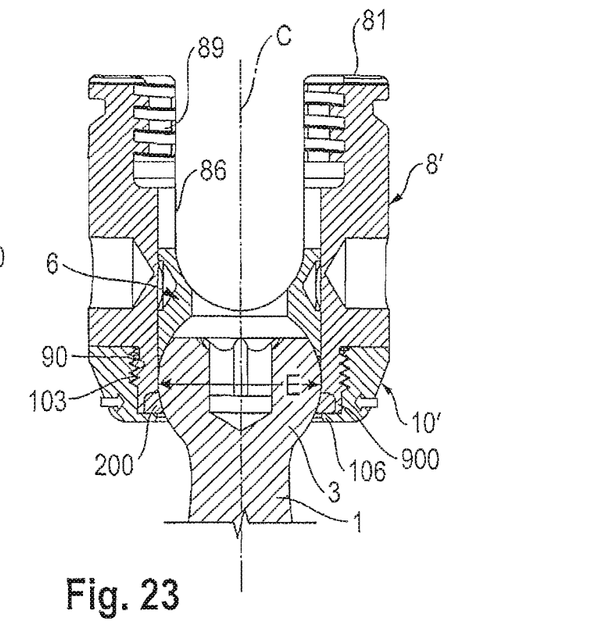
FIG. 23 shows a cross-sectional view of the polyaxial bone anchoring device according to the second embodiment in a fully assembled state.

The assembly of the polyaxial bone anchoring device according to the second embodiment will be described with reference to FIGS. 21 to 23. In a first step, the bone anchoring element 1 is inserted from the bottom end 82 into the upper member 8'. Then the lower member 10' with the pre-assembled clamping ring 200 is mounted from the bottom end 82 onto the upper member 8'. As shown in FIG. 21, the lower member 10' is screwed onto the upper member 8'. By further screwing the lower member 10' onto the upper member 8', the annular conical lower section 900 begins to contact the clamping ring 200 from above and penetrates into the space between the clamping ring 200 and the second portion 104' of the lower member 10, as depicted in particular in FIGS. 22a and 22b. Due to its conical shape, the lower section 900 increasingly compresses the clamping ring 200 in a radial direction so that the inner diameter of the clamping ring 200 decreases. Finally, as shown in FIG. 23, when the lower member 10' is fully mounted to the upper member 8', the clamping ring 200 is compressed to such an extent that it protrudes into the passage 85 of the upper member 8' and reduces the inner diameter of the passage 85 at a position below the greatest diameter E of the head 3. Hence, the head 3 is prevented from being removed through the bottom end 82. Simultaneously, the clamping ring 200 exerts a slight pressure onto the head 3, so that the head 3 is frictionally held between the clamping ring 200 and the protrusion 93 in an adjustable angular position.

Modifications of the previously described embodiments are conceivable. For example, while a plurality of bores 91 with balls 20 are shown, at east one bore with ball might be sufficient to achieve the function. While in the second embodiment, the lower portion 900 is shown as an annular portion, at least two or a plurality of distinct lug portions might be conceivable that exert pressure to compress the clamping ring. The protrusion 93 forming the stop for the head needs not be annular but can be realized through circumferentially distinct protrusions. Further, the protrusion needs not be spherically-shaped inside.

Instead of the balls or the clamping ring, other clamping devices are conceivable, such as, for example, spring elements that can be compressed while introducing the head and can extend when the head has passed their position and hold the head in place.

The outer contour of the upper member and the lower member is not limited to the outer contour shown in the embodiments. Also, instead of the threaded connection between the upper member and the lower member, a press-fit connection or any other connection that allows to fix the lower member to the upper member, is possible. The receiving part may also have a design that allows the bone anchoring element to be pivoted at a larger angle to one side compared to another side.

The locking element s not limited to the inner screw shown in the embodiments. Any kind of locking element or combination of locking elements, such as a two-part locking element, might be conceivable. Also, the pressure element is not limited to the specific shape shown in the embodiments. For example, the pressure element may have a U-shaped recess instead of a cylindrical recess, that provides a channel for the rod with legs extending above the rod so that a corresponding locking device may be used that allows to independently fix the head and the rod.

The bone anchoring element may be any suitable bone anchoring element, such as a bone screw, a bone nail, a bone anchor with barbs, a cannulated bone anchoring element, etc.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising a receiving part for receiving a head of a bone anchoring element and for receiving a rod, the receiving part comprising:
    a first member with a top end and a bottom end, a central axis extending through the top end and the bottom end, a head receiving portion having an inner wall defining a passage at the bottom end for accommodating the head of the bone anchoring element, and a channel at the top end for receiving the rod;
    a second member having a top end and a bottom end and a bore extending from the top end to the bottom end, the second member being connectable to the first member at or near the bottom end of the first member; and
    at least one clamping member that is separable from the first member and configured to be positioned at or near the bottom end of the first member and to protrude into the passage;
    wherein the second member is movable relative to the first member from a first position wherein the clamping member is movable radially between the position protruding into the passage and a position farther away from the central axis, to a second position wherein the clamping member is prevented from moving to the position farther away from the central axis to hold the head of the bone anchoring element in the head receiving portion, and wherein when the second member is at the second position, an engagement between the first member and the second member holds the second member against movement towards the first position.

2. The polyaxial bone anchoring device of claim 1, wherein the at least one clamping member is also movable in the radial direction relative to the central axis when the second member is not connected to the first member.

3. The polyaxial bone anchoring device of claim 1, wherein a plurality of clamping members are provided that are arranged in a circumferential direction around the central axis.

4. The polyaxial bone anchoring device of claim 3, wherein the clamping members comprise balls.

5. The polyaxial bone anchoring device of claim 4, wherein the balls are configured to be provided in bores of the first member that extend substantially transverse to the central axis.

6. The polyaxial bone anchoring device of claim 4, wherein the balls are configured to be rotatably held in the first member.

7. The polyaxial bone anchoring device of claim 4, wherein the balls are movable in respective radial directions transverse to the central axis in a limited manner.

8. The polyaxial bone anchoring device of claim 1, wherein the at least one clamping member comprises a clamping ring that is compressible in the radial direction.

9. The polyaxial bone anchoring device of claim 8, wherein the clamping ring comprises a slotted ring.

10. The polyaxial bone anchoring device of claim 8, wherein the clamping ring is configured to be arranged in the second member.

11. The polyaxial bone anchoring device of claim 8, wherein the first member comprises a clamping portion at or near the bottom end configured to cooperate with the clamping ring to compress the clamping ring when the second member is connected to the first member.

12. The polyaxial bone anchoring device of claim 1, wherein the at least one clamping member is secured against disassembling from other portions of the receiving part.

13. The polyaxial bone anchoring device of claim 1, wherein the first member and the second member are connectable by threads.

14. The polyaxial bone anchoring device of claim 1, further comprising the bone anchoring element having a shaft for anchoring in a bone and the head insertable into the head receiving portion of the first member.

15. The polyaxial bone anchoring device of claim 14, wherein the at least one clamping member is configured to exert a pressure force onto the head when the head is inserted in the head receiving portion and the second member is connected to the first member.

16. The polyaxial bone anchoring device of claim 14, wherein the first member comprises a stop in the passage for the head for preventing further insertion of the head into the first member.

17. The polyaxial bone anchoring device of claim 16, wherein the stop is at a distance from the bottom end of the first member, such that when the head abuts against the stop, the at least one clamping member is positioned below a region of the head with a greatest diameter in an axial direction.

18. The polyaxial bone anchoring device of claim 14, further comprising a pressure element, wherein when the head is in the head receiving portion, the pressure element is configured to exert pressure onto the head on a side opposite the clamping member relative to a greatest diameter of the head.

19. The polyaxial bone anchoring device of claim 1, wherein the second member is positioned on an outside of the clamping member in a radial direction.

20. A method for coupling a rod to a bone via a polyaxial bone anchoring device, the bone anchoring device comprising a bone anchoring element having a shaft for anchoring in a bone and a head, a receiving part comprising a first member with a top end and a bottom end, a central axis extending through the top end and the bottom end, a head receiving portion having an inner wall defining a passage at the bottom end for accommodating the head, and a channel at the top end for receiving the rod, a second member having a top end and a bottom end and a bore extending from the top end to the bottom end, the second member being connectable to the first member at or near the bottom end of the first member, at least one clamping member that is separable from the first member and configured to be positioned at or near the bottom end of the first member and to protrude into the passage, and a locking element, wherein the second member is movable relative to the first member from a first position wherein the clamping member is movable radially between the position protruding into the passage and a position farther away from the central axis, to a second position wherein the clamping member is prevented from moving to the position farther away from the central axis to hold the head in the head receiving portion, and wherein when the second member is at the second position, an engagement between the first member and the second member holds the second member against movement towards the first position, the method comprising:
  inserting the bone anchoring element into a bone;
    adjusting an angular position of the bone anchoring element relative to the receiving part;
    inserting the rod into the channel of the receiving part; and
    advancing the locking element in the receiving part to lock the angular position of the bone anchoring element and a position of the rod relative to the receiving part.

21. The method of claim 20, further comprising:
inserting the head into the head receiving portion of the first member; and
connecting the second member to the first member and moving the second member to the second position to prevent the clamping member from moving to the position farther away from the central axis and to hold the head in the receiving part.

22. A polyaxial bone anchoring device comprising:
a bone anchoring element having a shaft for anchoring in a bone and a head; and
a receiving part for receiving the head of the bone anchoring element and for receiving a rod, the receiving part comprising:
  a first member with a top end and a bottom end, a central axis extending through the top end and the bottom end, a head receiving portion having an inner wall defining a passage at the bottom end for accommodating the head of the bone anchoring element, and a channel at the top end for receiving the rod;
  a second member having a top end and a bottom end and a bore extending from the top end to the bottom end, the second member being connectable to the first member at or near the bottom end of the first member; and
  at least one clamping member that is separable from the first member and configured to be positioned at or near the bottom end of the first member and to protrude into the passage;
wherein the second member is movable relative to the first member from a first position wherein the clamping member is movable radially between the position protruding into the passage and a position farther away from the central axis, to a second position wherein the clamping member is configured to contact the head of the bone anchoring element and is prevented from moving to the position farther away from the central axis to hold the head of the bone anchoring element in the head receiving portion, and wherein when the second member is at the second position, an engagement between the first member and the second member holds the second member against movement towards the first position.

23. The polyaxial bone anchoring device of claim 22, wherein the head of the bone anchoring element is insertable into the passage through the bottom end of the first member.

* * * * *